United States Patent
Yan

(10) Patent No.: US 9,330,451 B2
(45) Date of Patent: May 3, 2016

(54) METHOD AND APPARATUS FOR DETECTING DEFECT OF BACKLIGHT MODULE

(71) Applicant: BOE OPTICAL SCIENCE AND TECHNOLOGY CO., LTD., Suzhou, Jiangsu (CN)

(72) Inventor: David Yan, Beijing (CN)

(73) Assignees: BOE Optical Science and Technology Co., Ltd, Suzhou (CN); BOE Technology Group Co., Ltd, Beijing (CN)

( * ) Notice: Subject to any disclaimer, the term of this patent is extended or adjusted under 35 U.S.C. 154(b) by 129 days.

(21) Appl. No.: 14/346,868

(22) PCT Filed: May 31, 2013

(86) PCT No.: PCT/CN2013/076536
§ 371 (c)(1),
(2) Date: Mar. 24, 2014

(87) PCT Pub. No.: WO2014/134880
PCT Pub. Date: Sep. 12, 2014

(65) Prior Publication Data
US 2015/0063675 A1   Mar. 5, 2015

(30) Foreign Application Priority Data
Mar. 6, 2013 (CN) .......................... 2013 1 0071403

(51) Int. Cl.
G06K 9/00 (2006.01)
G06T 7/00 (2006.01)
(Continued)

(52) U.S. Cl.
CPC ............. *G06T 7/001* (2013.01); *G01M 11/081* (2013.01); *G01N 21/8806* (2013.01); *G01N 21/95* (2013.01); *G06T 7/0004* (2013.01); *G09G 3/006* (2013.01); *G09G 3/3406* (2013.01); *G06T 2207/10016* (2013.01); *G06T 2207/30164* (2013.01); *G09G 2330/10* (2013.01)

(58) Field of Classification Search
None
See application file for complete search history.

(56) References Cited

U.S. PATENT DOCUMENTS

| 6,965,120 B1 | 11/2005 | Beyerer et al. | |
| 8,602,603 B2 * | 12/2013 | Fang | G02B 6/0073 362/311.01 |

(Continued)

FOREIGN PATENT DOCUMENTS

| CN | 1996441 A | 7/2007 |
| CN | 101261234 A | 9/2008 |

(Continued)

OTHER PUBLICATIONS

Computer English Translation of Chinese Patent No. CN102645765A, pp. 1-5, Aug. 2012.*

(Continued)

*Primary Examiner* — Daniel Mariam
(74) *Attorney, Agent, or Firm* — Banner & Witcoff, Ltd.

(57) ABSTRACT

According to embodiments of the invention, there are disclosed a method and an apparatus for detecting defect of a backlight module. Images that show components in the backlight module are acquired with a plurality of preset angles relative to a surface of the backlight module. The acquired images that show the components in the backlight module are analyzed, so as to determine whether a defect presents in the components in the backlight module.

13 Claims, 6 Drawing Sheets

(51) Int. Cl.
*G01M 11/08* (2006.01)
*G09G 3/00* (2006.01)
*G01N 21/88* (2006.01)
*G01N 21/95* (2006.01)
*G09G 3/34* (2006.01)

(56) References Cited

U.S. PATENT DOCUMENTS

2005/0018897 A1  1/2005  Choi et al.
2010/0157044 A1  6/2010  Mori et al.
2012/0249753 A1  10/2012  Tsai et al.

FOREIGN PATENT DOCUMENTS

| CN | 101419176 A | 4/2009 |
| CN | 101419176 B | 3/2012 |
| CN | 102739952 A | 10/2012 |
| TW | 200722825 | 12/1994 |
| TW | I321650 B | 3/2010 |
| TW | 201027067 A | 7/2010 |

OTHER PUBLICATIONS

Coputer English Translation of Chinese Patent No. TW200722825, pp. 1-11, Jun. 2007.*
Computer English Translation of Chinese Patent No. TWi321650B, pp. 1-8, Mar. 2010.*
International Search Report for International Application No. PCT/CN2013/076536 dated Oct. 24, 2013.
First Office Action issued by the Chinese Patent Office for Chinese Patent Application No. 2013100714030 dated Sep. 3, 2014, 9pgs.
English translation of First Office Action issued by the Chinese Patent Office for Chinese Patent Application No. 2013100714030 dated Sep. 3, 2014, 10pgs.
Sep. 8, 2015—International Preliminary Report on Patentability Appn PCT/CN2013/076536.

* cited by examiner

METHOD AND APPARATUS FOR DETECTING DEFECT OF BACKLIGHT MODULE

CROSS REFERENCE TO RELATED APPLICATIONS

This application is based on International Application No. PCT/CN2013/076536 filed on May 31, 2013, which claims priority to Chinese National Application No. 201310071403.0 filed on Mar. 6, 2013. The entire contents of each and every foregoing application are incorporated herein by reference.

TECHNICAL FIELD

Embodiments of the invention relate to a technical field of defect detection, and particularly, to a method and an apparatus for detecting defect of a backlight module.

BACKGROUND

Electronic products with a display function that are used currently, such as televisions, displays, digital cameras, mobile phones, PDAs, portable DVDs, etc, are each configured to display video signals with a liquid crystal panel, and the display effect of the liquid crystal panel is greatly dependent on the light source design and quality of a backlight module. The backlight module may directly affect the display effect and the image contrast of the liquid crystal panel, and therefore, the image display quality of the liquid crystal panel will be improved by providing the backlight module with a good performance.

In the fabricating process of the backlight module, it is necessary to defect whether the backlight module has a defect, such as scratch, foreign matter, stain, white spot, light leakage, etc. In a conventional detection method, the backlight module is firstly placed on a fixture and turned on, namely, the backlight module is lit, and then the backlight module is inspected by eyes of a worker. If there exits the defect, a marking is made at the defect location, and thereafter, the product with the defect is sent to a repair workshop. Since the above-described conventional detection method detects the defect in a manual manner, the work efficiency is low, the miss rate is relatively high, and accordingly this conventional detection method can not be applied to the mass production to achieve a satisfying quantitative detection.

In addition, if the backlight module is detected with an existing mechanical detection apparatus, only defects on the appearance of the backlight module can be detected and the defects inside the backlight module can not be detected.

SUMMARY OF THE INVENTION

According to embodiments of the invention, there are provided a method and an apparatus for detecting defect of a backlight module, so as to detect the defects on the appearance of the backlight module as well as the defects inside the backlight module with high efficiency.

According to an embodiment of the invention, there is provided a detection method for detecting defect of a backlight module. The method comprises: acquiring images that show components in the backlight module with a plurality of preset angles relative to a surface of the backlight module; and analyzing the acquired images that show the components in the backlight module, so as to determine whether a defect presents in the components in the backlight module.

According to an embodiment of the invention, there is provided a detection apparatus for detecting defect of a backlight module. The apparatus comprises: a stand; a defect detection device mounted on the stand, and a carrier mounted on the stand and used for bearing the backlight module. The defect detection device comprises: an image acquiring unit, used for acquiring images that show components in the backlight module with a plurality of preset angles relative to a surface of the backlight module; and an image analyzing unit, communicated with the image acquiring unit, and used for analyzing the acquired images that show the components in the backlight module so as to determine whether a defect presents in the components in the backlight module.

DESCRIPTION OF THE EMBODIMENTS

Hereinafter, a method and an apparatus for detecting defect of a backlight module according to embodiments of the invention will be described in detail in combination with accompanied drawings.

Figure 8:
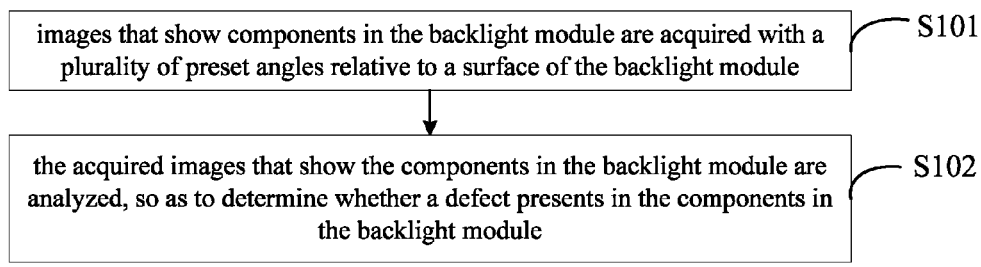
FIG. 8(*a*) and FIG. 8(*b*) illustrate a detection method for detecting defect of a backlight module according to an embodiment of the invention.
Figure 8:
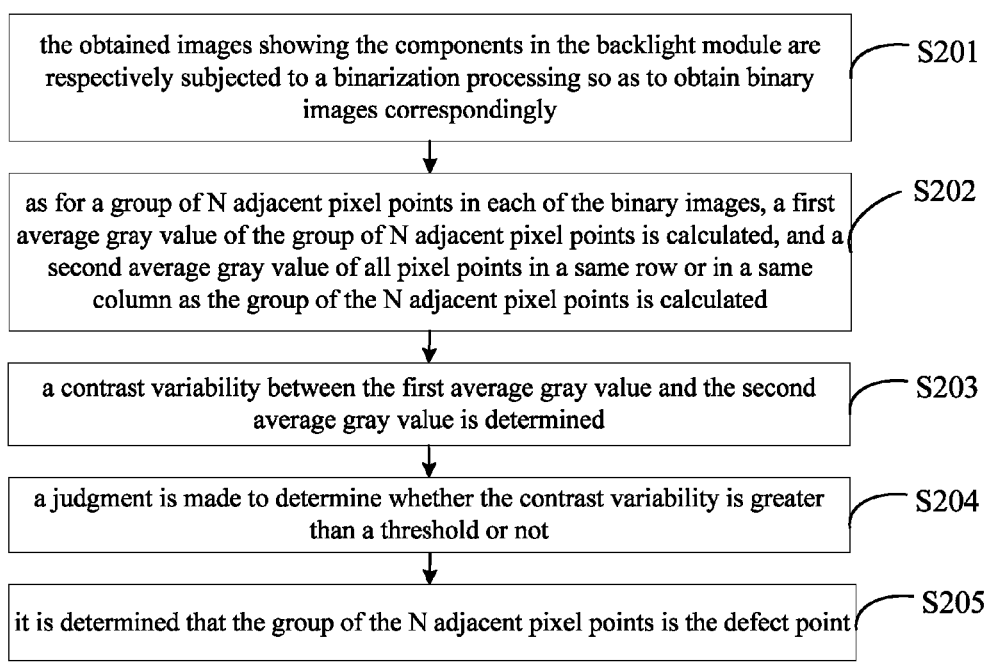

According to an embodiment of the invention, as shown in FIG. 8(*a*), the detection method for detecting defect of the backlight module may include the following steps:

S101, images that show components in the backlight module are acquired with a plurality of preset angles relative to a surface of the backlight module;

S102, the acquired images that show the components in the backlight module are analyzed, so as to determine whether a defect presents in the components in the backlight module.

The backlight module generally comprises a light guide plate, a diffusion plate, optical films such as a reflector film and a brightness enhancement film, and the like. With different illumination modes and at different photographing angles, images that can clearly exhibit the defect on components in the backlight module can be acquired. When an external light source is used to illuminate the surface of the backlight module, the smaller an angle between a photographing direction and the surface of the backlight module is, the better the defect of a component near the surface of the backlight module can be presented by the acquired images. In the above detection method according to the embodiment of the invention, by way of obtaining images at different preset angles, images showing components in the backlight module can be acquired; and after the images are analyzed, the defect point present in the components can be determined. Accordingly, the defects on the appearance of the backlight module as well as the defects inside the backlight module can be detected. Furthermore, with the detection method for detecting defect of the backlight module according to the embodiment of the invention, the detection efficiency and the detection accuracy can be improved as compared to the conventional technology of detecting the defect of the backlight module manually.

Hereinafter, the examples for implementing the above detection method according to the embodiment of the invention will be described in detail.

The step S101 of acquiring images that show components in the backlight module with a plurality of preset angles relative to a surface of the backlight module in the above method according to the embodiment of the invention may be performed as follows.

(1) when an image showing an appearance of the backlight module needs to be acquired, the following steps may be performed: illuminating the backlight module at a first preset angle by an external light source, and acquiring the image showing the surface of the backlight module with a second preset angle relative to the surface of the backlight module.

For example, the external light source is a white light source, which has a better effect than other light sources such as green light source. For example, the first preset angle at which the backlight module is illuminated by the external light source is 45°. Further, for example, the second preset angle with which the image showing the surface of the backlight module is acquired is 90°.

(2) when an image showing a light guide plate in a lowest layer of the backlight module needs to be acquired, the following steps may be performed: lighting (that is, turning on) the backlight module, and acquiring the image showing the light guide plate in the backlight module with a third preset angle relative to the surface of the backlight module. At this time, no external light source illuminates the backlight module.

For example, the third preset angle with which the image showing the light guide plate in the backlight module is acquired is 90°.

(3) when an image showing other components than the light guide plate in the backlight module needs to be acquired, the following steps may be performed: illuminating the backlight module at the first preset angle by the external light source, and acquiring the image showing a diffusion plate or an optical film in the backlight module with a fourth preset angle relative to the surface of the backlight module.

For example, the external light source is the white light source, which has a better effect than other light sources such as green light source. For example, the first preset angle at which the backlight module is illuminated by the external light source is 45°. Further, for example, the fourth preset angle with which the image showing the diffusion plate or the optical film in the backlight module is acquired is 60° or 30°.

After the images showing respective components in the backlight module are obtained, the images showing the respective components in the backlight module are analyzed in the step S102, so as to determine whether the defect presents in the components in the backlight module. For example, as shown in FIG. 8(b), the step S102 may be performed as follows.

S201, the obtained images showing the components in the backlight module are respectively subjected to a binarization processing so as to obtain binary images correspondingly. The binarization processing is well-known to those skilled in the art, and thus details thereof are omitted here.

S202, as for a group of N adjacent pixel points in each of the binary images, a first average gray value of the group of N adjacent pixel points is calculated, and a second average gray value of all pixel points in a same row or in a same column as the group of the N adjacent pixel points is calculated. N is a positive integer.

For example, three pixel points that are adjacent in the binary image is taken as one group, and the first average gray value of the three adjacent pixel points is calculated. The three adjacent pixel points may be in the same row, or may be in the same column, and no limitation will be made here. When the three adjacent pixel points are in the same row, the second average gray value of all pixel points in the same row as the group of the three adjacent pixel points is calculated. Similarly, when the three adjacent pixel points are in the same column, the second average gray value of all pixel points in the same column as the group of the three adjacent pixel points is calculated.

S203, a contrast variability between the first average gray value and the second average gray value is determined.

The calculation formula of the contrast variability is: contrast variability=|the first average gray value−the second average gray value|/the second average gray value.

S204, a judgment is made to determine whether the contrast variability is greater than a threshold or not. If it is judged that the contrast variability is greater than the threshold, the step S205 is executed. If it is judged that the contrast variability is not greater than the threshold, the detection method returns to the step S202 and makes the calculation related with other group of N adjacent pixel points.

S205, it is determined that the group of the N adjacent pixel points is the defect point.

After it is determined that the group of the N adjacent pixel points is the defect point, the location of the defect point is recorded so as to facilitate the subsequent repair process.

After the defect point present in components in the backlight module has been determined, the above detection method according to the embodiment of the invention may further include a step of judging and determining a type of the defect point. For example, this step may be performed as follows.

Geometrical feature parameters of at least one feature pattern formed by all defect points present in the components in the backlight module are calculated, and the defect type of the feature pattern is determined according to the calculated geometrical feature parameters of the feature pattern.

For example, a simplified PCNN (Pulse Coupled Neural Network) model may be used. Firstly, the images of components that have been judged to have the defect point are subjected to a binary segmentation processing. For example, the pixel value of the pixel point at which the defect point is located is labeled as 1, and the pixel value of other pixel points are labeled as 0.

Figure 1:
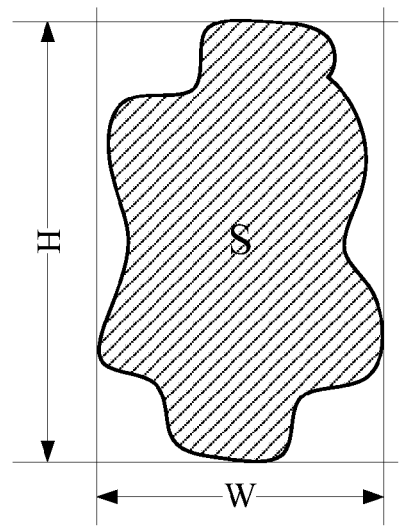
FIG. 1 is a schematic view illustrating a feature pattern according to an embodiment of the invention.

Next, geometrical feature parameters, such as area, width, height and so on, of the region of the feature pattern formed by the consecutive defect points are calculated. For example, as shown in FIG. 1, the number of the pixel points that have the pixel value of 1 in the feature pattern is counted, and this number is recorded as area S of the feature pattern. The number of pixel points that have the pixel value of 1 from the leftmost end to the rightmost end of the feature pattern is counted, and this number is recorded as width W of the feature pattern. The number of pixel points that have the pixel value of 1 from the uppermost end to the lowest end of the feature pattern is counted, and this number is recorded as height H of the feature pattern.

After the geometrical feature parameters of the feature pattern have been calculated, the geometrical feature parameters of the feature pattern are compared with features of various defect types stored in a database, so as to obtain the defect type of the feature pattern.

In addition, if it is found that features of various defect types stored in the database do not conform to the geometrical feature parameters of the feature pattern or no defect type corresponding to the geometrical feature parameters of the feature pattern is stored in the database, the data stored in the database may be modified or a new data corresponding to the geometrical feature parameters of the feature pattern is added to the database.

Based on the similar idea, a detection apparatus for detecting defect of a backlight module is further provided according to an embodiment of the invention. Since the principle of the detection apparatus is similar to that of the aforesaid detection method for detecting defect of the backlight module, the implementation of the detection apparatus may refer to the implementation of the detection method, and repeated descriptions will be omitted.

Figure 2:
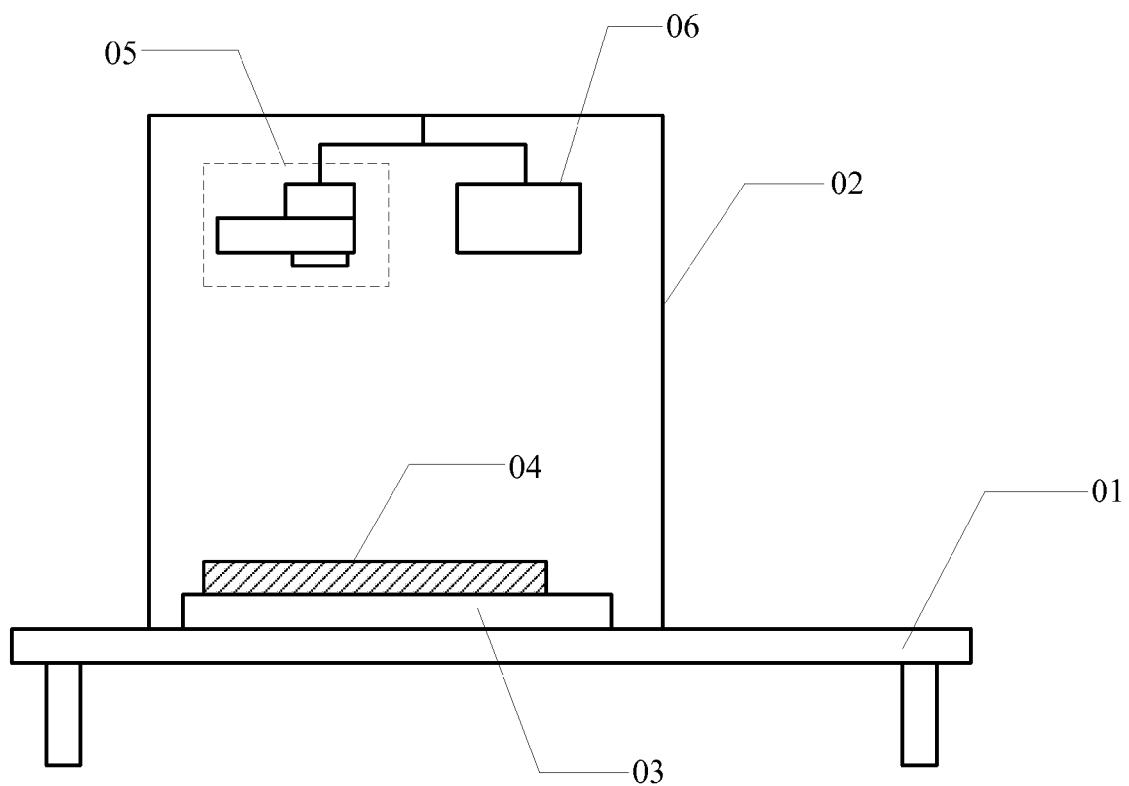
FIG. 2 is a structurally schematic view illustrating a detection apparatus for detecting defect of a backlight module according to an embodiment of the invention.

As shown in FIG. 2, the detection apparatus for detecting defect of the backlight module according to the embodiment of the invention includes: a stand 01, a defect detection device 02 mounted on the stand 01, and a carrier 03 mounted on the stand 01 and used for bearing the backlight module 04.

The defect detection device 02 comprises: an image acquiring unit 05, used for acquiring images that show components in the backlight module 04 with a plurality of preset angles relative to a surface of the backlight module 04; and an image analyzing unit 06, communicated with the image acquiring unit 05, and used for analyzing the acquired images that show components in the backlight module 04 so as to determine whether a defect presents in the components in the backlight module 04.

The preset angles between the image acquiring unit 05 and the surface of the backlight module 04 may be 90°, 60° or 30°, so as to acquire the images that show the respective components in the backlight module 04.

Generally, the backlight module 04 comprises a light guide plate, a diffusion plate, optical films such as a reflector film and a brightness enhancement film, and the like.

When an image showing an appearance of the backlight module 04 needs to be acquired, the following steps may be performed: illuminating the backlight module 04 at a first preset angle by an external light source, and acquiring the image showing the surface of the backlight module with an angle of 90° relative to the surface of the backlight module by the image acquiring unit 05. For example, the external light source is a white light source, which has a better effect than other light sources such as green light source. For example, the first preset angle at which the backlight module is illuminated by the external light source is 45°.

When an image showing a light guide plate in a lowest layer of the backlight module needs to be acquired, the following steps may be performed: lighting the backlight module 04, and acquiring the image showing the light guide plate in the backlight module with an angle of 90° relative to the surface of the backlight module by the image acquiring unit 05. At this time, no external light source illuminates the backlight module.

When an image showing other components than the light guide plate in the backlight module needs to be acquired, the following steps may be performed: illuminating the backlight module at the first preset angle by the external light source, and acquiring the image showing the diffusion plate or the optical film in the backlight module with an angle of 30° or 60° relative to the surface of the backlight module by the image acquiring unit 05.

Hereinafter, the structure examples of the defect detection device in the above detection apparatus according to the embodiment of the invention will be described.

Example 1

Figure 3:
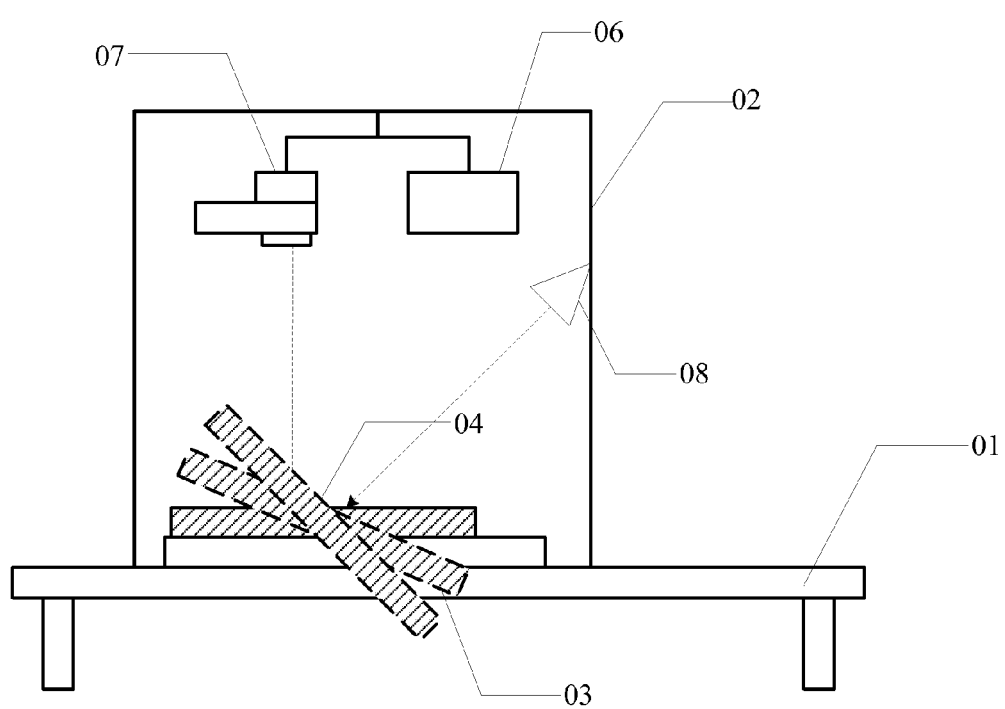
FIG. 3 is a structurally schematic view illustrating an example 1 according to an embodiment of the invention.

As shown in FIG. 3, the defect detection device 02 has one detection station.

The image acquiring unit includes one CCD (Charge Coupled Device) 07 located at the detection station.

In addition, at the detection station, there is an external light source 08 for illuminating the backlight module 04. The external light source 08 usually illuminates the surface of the backlight module 04 at an angle of 45°.

The carrier 03 is a carrier that is capable of turning over along an axis parallel to a surface of the carrier 03. In this way, in the case that images showing components in the backlight module 03 are acquired at different preset angles, the angle between the photographing direction of the CCD 07 and the surface of the backlight module 04 can be adjusted by rotating the carrier 03 and the backlight module 04 provided on it.

Example 2

Figure 4:
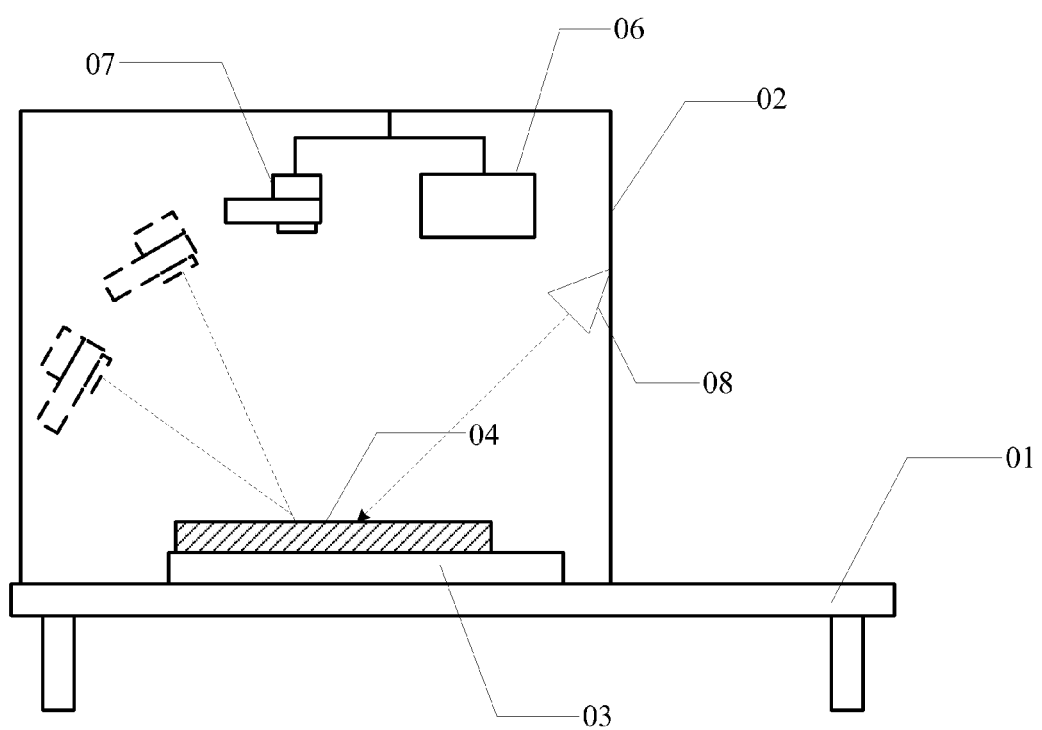
FIG. 4 is a structurally schematic view illustrating an example 2 according to an embodiment of the invention.

As shown in FIG. 4, the defect detection device 02 has one detection station.

In addition, at the detection station, there is an external light source 08 for illuminating the backlight module 04. The external light source 08 usually illuminates the surface of the backlight module 04 at an angle of 45°.

The image acquiring unit includes one CCD 07 located at the detection station, and an angle between the photographing direction of the CCD 07 and the surface of the backlight module 04 is adjustable. In this way, in the case that images showing components in the backlight module 04 are acquired at different preset angles, the relative position between the CCD 07 and the backlight module 04 can be adjusted by rotating the CCD 07.

Example 3

Figure 5:
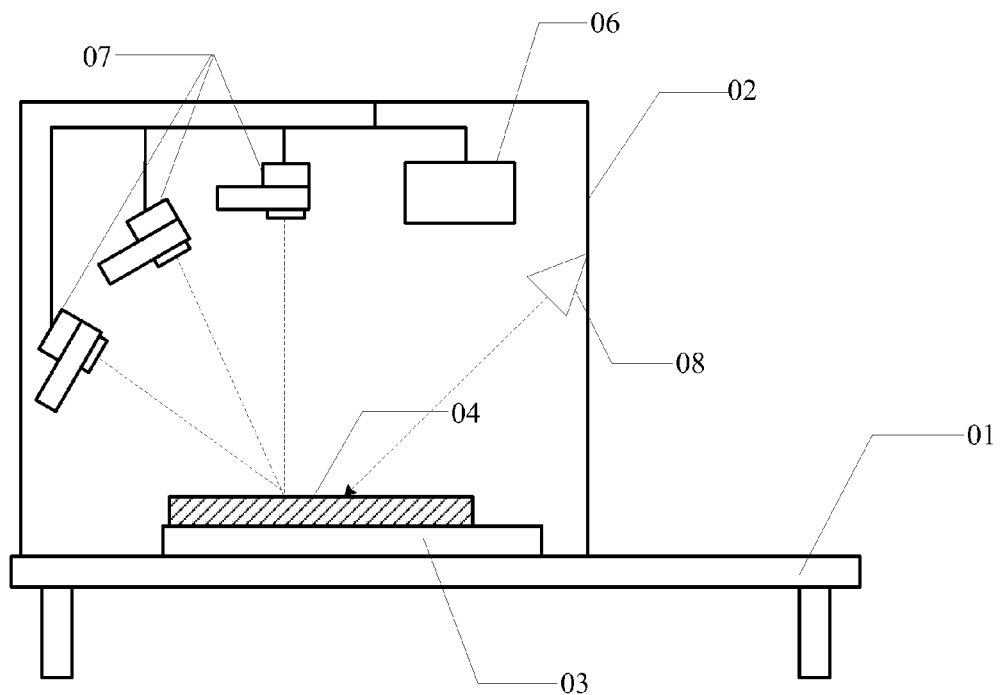
FIG. 5 is a structurally schematic view illustrating an example 3 according to an embodiment of the invention.

As shown in FIG. 5, the defect detection device 02 has one detection station.

In addition, at the detection station, there is an external light source 08 for illuminating the backlight module 04. The external light source 08 usually illuminates the surface of the backlight module 04 at an angle of 45°.

The image acquiring unit includes a plurality of CCDs 07 located at the detection station, and angles between photographing directions of the plurality of CCDs 07 and the surface of the backlight module 04 are different from one another. In this way, images showing components in the backlight module 04 can be obtained simultaneously by the plurality of CCDs 07 with different preset angles.

Example 4

Figure 6:
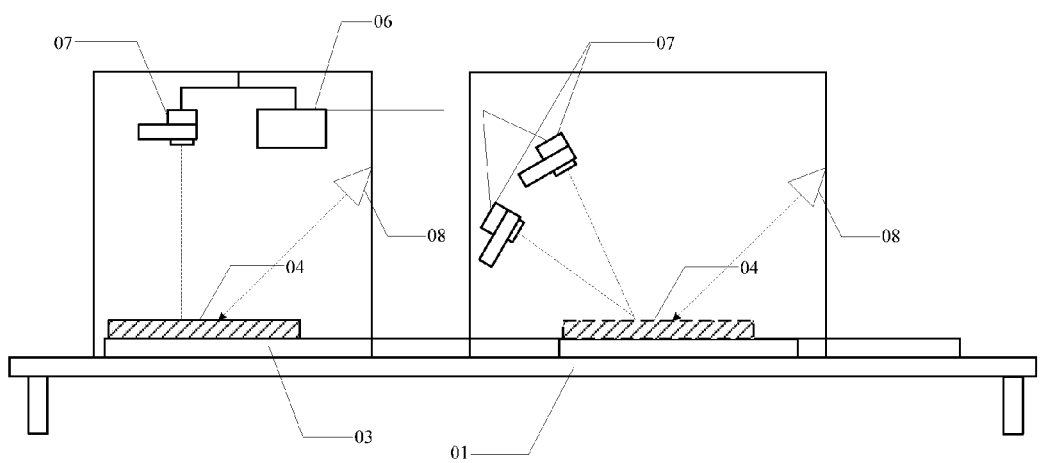
FIG. 6 is a structurally schematic view illustrating an example 4 according to an embodiment of the invention.

As shown in FIG. 6, the carrier 03 is mounted on the stand 01 via a transport device.

The defect detection device has a plurality of detection stations located on the travel route of the transport device.

In addition, for at least one of the detection stations, there is provided an external light source 08 for illuminating the backlight module 04. The external light source 08 usually illuminates the surface of the backlight module 04 at an angle of 45°.

The image acquiring unit includes at least one CCD 07 provided for each detection station, and the angles between photographing directions of the CCDs 07 and the surface of the backlight module 04 is two angles at least.

For example, at one detection station, there may be provided one CCD 07 or there may be provided a plurality of CCDs 07, and no limitation will be made here. Photographing directions of the CCDs 07 may be different from one another or may be the same in part, and no limitation will be made here.

By adopting multiple detection stations and multiple CCDs in Example 4, detection without pause can be achieved, and thereby the detection efficiency can be improved.

Furthermore, the CCD (or CCDs) 07 mentioned in Example 1, Example 2, Example 3 and Example 4 may be linear array CCD (or CCDs), or may be planar array CCD (or CCDs), and no limitation will be made here.

Figure 7:
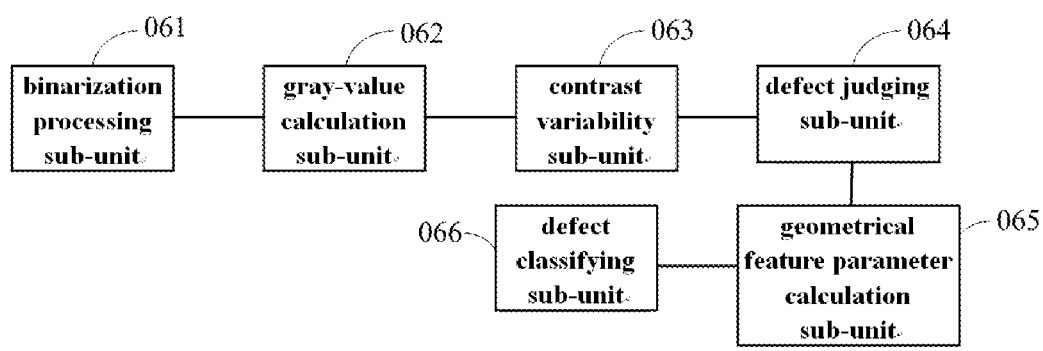
FIG. 7 is a structurally schematic view illustrating an image analyzing unit according to an embodiment of the invention.

As shown in FIG. 7, the image analyzing unit 06 in the aforesaid detection apparatus according to the embodiment of the invention may include:

A binarization processing sub-unit 061, communicated with the image acquiring unit 05 and used for performing the binarization processing on the obtained images that show components in the backlight module, respectively, so as to correspondingly obtain binary images;

A gray-value calculation sub-unit 062, communicated with the binarization processing sub-unit 061, and used for determining a first average gray-value of a group of N adjacent pixel points in each of the binary images and calculating a second average gray-value of all pixel points in a same row or in a same column as the group of N adjacent pixel points;

A contrast variability sub-unit 063, communicated with the gray-value calculation sub-unit 062, and used for determining a contrast variability between the first average gray-value and the second average gray-value;

A defect judging sub-unit 064, communicated with the contrast variability sub-unit 063, and used for determining that the group of the N adjacent pixel points is the defect point when the contrast variability is greater than a threshold.

Further, as shown in FIG. 7, the image analyzing unit 06 in the aforesaid detection apparatus according to the embodiment of the invention may further include:

A geometrical feature parameter calculation sub-unit 065, communicated with the defect judging sub-unit 064, and used for calculating geometrical feature parameters of at least one feature pattern formed by all defect points present in components in the backlight module; and A defect classifying sub-unit 066, communicated with the geometrical feature parameter calculation sub-unit 065, and used for determining the defect type of the feature pattern according to the calculated geometrical feature parameters of the feature pattern.

Through descriptions of the above embodiments, those skilled in the art can clearly understand that, embodiments of the invention can be implemented by hardware, or can be implemented by means of software, and if necessary, by way of a hardware platform. Based on this understanding, the embodiments of the invention can be embodied in the form of software products. The software products may be stored in a non-volatile storage medium (such as, a CD-ROM, a U-disk, a portable hard disk, or the like), and include a number of instructions to instruct a computer equipment (such as, a personal computer, a server, a network equipment, or the like) to execute the method as stated in each embodiment of the invention.

Those skilled in the art can understand that, the accompanied drawings merely schematically show the preferred embodiments of the invention, and modules or procedures in the accompanied drawings are not necessarily indispensable to achieve the invention.

Those skilled in the art can understand that, the module in the apparatus in one embodiment may be distributed in the apparatus of the embodiment in accordance with description of the embodiment, or may be changed to be located in one or a plurality of apparatuses different from the embodiment. Modules in the above embodiments may be merged into one module, or may be divided into multiple sub-modules.

The above numbering of embodiments and examples of the invention is merely for the sake of description, and does not represent superiority or inferiority of the embodiments and examples.

In the detection method for detecting defect of the backlight module according to an embodiment of the invention, images that show the components in the backlight module are acquired with the plurality of preset angles relative to the surface of the backlight module, and the acquired images that show the components in the backlight module are analyzed, so as to determine whether the defect presents in the components in the backlight module. By way of obtaining the images at the different preset angles, images that show the components in the backlight module can be acquired; and after the images are analyzed, whether the defect point presents in the components can be determined, so as to realize the detection of the defects on the appearance of the backlight module as well as the defects inside the backlight module. Furthermore, with the detection method for detecting defect of the backlight module according to embodiments of the invention, the detection efficiency and the detection accuracy can be improved as compared to the conventional technology of detecting the defect of the backlight module manually.

The detection apparatus for detecting defect of the backlight module according to an embodiment of the invention includes the defect detection device mounted on the stand and the carrier mounted on the stand and used for bearing the backlight module. The defect detection device comprises: the image acquiring unit, used for acquiring the images that show the components in the backlight module with the plurality of preset angles relative to the surface of the backlight module; and the image analyzing unit, communicated with the image acquiring unit, and used for analyzing the acquired images that show the components in the backlight module so as to determine whether the defect presents in the components in the backlight module. Because the image acquiring unit adopts a way of obtaining the images from different preset angles, the images that show the components in the backlight module can be obtained. After the images are analyzed by the image analyzing unit, whether the defect point present in the components can be determined, so as to realize the detection of the defects on the appearance of the backlight module as well as the defects inside the backlight module. Furthermore, with the detection apparatus for detecting defect of the backlight module according to embodiments of the invention, the detection efficiency and the detection accuracy can be improved as compared to the conventional technology of detecting the defect of the backlight module manually.

Obviously, various modifications and variants of the invention can be made by those skilled in the art without departing from the spirit and scope of the invention. As such, provided that these modifications and variants of the invention fall into the scope of claims of the invention and their equivalent technologies, it is intended by the invention to embrace these modifications and variants therein.

What is claimed is:

1. A detection method for detecting defect of a backlight module, comprising:
   acquiring images that show components in the backlight module with a plurality of preset angles relative to a surface of the backlight module; and
   analyzing the acquired images that show the components in the backlight module, so as to determine whether a defect presents in the components in the backlight module,
   wherein, the analyzing the acquired images that show the components in the backlight module so as to determine whether the defect present in the components in the backlight module includes:
   performing a binarization processing on the acquired images that show the components in the backlight module, respectively, so as to obtain binary images correspondingly;
   as for a group of N adjacent pixel points in each of the binary images, calculating a first average gray value of the group of the N adjacent pixel points, and calculating a second average gray value of all pixel points in a same row or in a same column as the group of the N adjacent pixel points, wherein N is a positive integer;
   determining contrast variability between the first average gray value and the second average gray value; and
   when it is judged that the contrast variability is greater than a threshold, determining that the group of the N adjacent pixel points is the defect.

2. The detection method of claim 1, wherein, the acquiring the images that show the components in the backlight module with the plurality of preset angles relative to the surface of the backlight module includes:
   illuminating the backlight module at a first preset angle with an external light source, and acquiring an image showing the surface of the backlight module with a second preset angle relative to the surface of the backlight module;
   lighting the backlight module, and acquiring an image showing a light guide plate in the backlight module with a third preset angle relative to the surface of the backlight module; and
   illuminating the backlight module at the first preset angle with the external light source, and acquiring an image showing a diffusion plate or an optical film in the backlight module with a fourth preset angle relative to the surface of the backlight module.

3. The detection method of claim 1, wherein, after determining that the defect presents in the components of the backlight module, the detection method further includes:
   calculating geometrical feature parameters of at least one feature pattern formed by all defects present in the components in the backlight module; and determining a defect type of the feature pattern according to the calculated geometrical feature parameters of the feature pattern.

4. A detection apparatus for detecting defect of a backlight module, comprising: a stand; a defect detection device mounted on the stand, and a carrier mounted on the stand and used for bearing the backlight module; wherein,
   the defect detection device comprises:
   an image acquiring unit, used for acquiring images that show components in the backlight module with a plurality of preset angles relative to a surface of the backlight module; and
   an image analyzing unit, communicated with the image acquiring unit, and used for analyzing the acquired images that show the components in the backlight module so as to determine whether a defect presents in the components in the backlight module,
   wherein, the image analyzing unit includes:
   a binarization processing sub-unit, communicated with the image acquiring unit and used for performing a binarization processing on the acquired images that show the components in the backlight module, respectively, so as to obtain binary images correspondingly;
   a gray-value calculation sub-unit, communicated with the binarization processing sub-unit, and used for determining a first average gray-value of a group of N adjacent pixel points in each of the binary images and calculating a second average gray-value of all pixel points in a same row or in a same column as the group of the N adjacent pixel points;
   a contrast variability sub-unit, communicated with the gray-value calculation sub-unit, and used for determining a contrast variability between the first average gray-value and the second average gray-value;
   a defect judging sub-unit, communicated with the contrast variability sub-unit, and used for determining that the group of the N adjacent pixel points is the defect when the contrast variability is greater than a threshold.

5. The detection apparatus of claim 4, wherein, the preset angles includes: 90°, 60° and 30°.

6. The detection apparatus of claim 4, wherein,
   the defect detection device has one detection station;
   the image acquiring unit includes one CCD located at the detection station;
   at the detection station, there is an external light source for illuminating the backlight module; and
   the carrier is a carrier arranged to turn over along an axis parallel to a surface of the carrier.

7. The detection apparatus of claim 4, wherein,
   the defect detection device has one detection station;
   the image acquiring unit includes one CCD located at the detection station, and an angle between a photographing direction of the CCD and the surface of the backlight module is adjustable; and
   at the detection station, there is an external light source for illuminating the backlight module.

8. The detection apparatus of claim 4, wherein,
   the defect detection device has one detection station;
   the image acquiring unit includes a plurality of CCDs located at the detection station, and angles between photographing directions of the plurality of CCDs and the surface of the backlight module are different from one another;
   at the detection station, there is an external light source for illuminating the backlight module.

9. The detection apparatus of claim 4, wherein,
   the carrier is mounted on the stand via a transport device;
   the defect detection device has a plurality of detection stations located on a travel route of the transport device;
   for at least one of the detection stations, there is provided an external light source for illuminating the backlight module;
   the image acquiring unit includes at least one CCD provided for each detection station, and angles between photographing directions of the CCDs and the surface of the backlight module is two angles at least.

10. The detection apparatus of claim 4, wherein, the image analyzing unit further includes:
    a geometrical feature parameter calculation sub-unit, communicated with the defect judging sub-unit, and used for calculating geometrical feature parameters of at least one feature pattern formed by all defects present in components in the backlight module; and a defect classifying sub-unit, communicated with the geometrical feature parameter calculation sub-unit, and used for determining a defect type of the feature pattern according to the calculated geometrical feature parameters of the feature pattern.

11. A detection method for detecting defect of a backlight module, comprising:

acquiring images that show components in the backlight module with a plurality of preset angles relative to a surface of the backlight module; and analyzing the acquired images that show the components in the backlight module, so as to determine whether a defect presents in the components in the backlight module, wherein, the acquiring the images that show the components in the backlight module with the plurality of preset angles relative to the surface of the backlight module includes:

illuminating the backlight module at a first preset angle with an external light source, and acquiring an image showing the surface of the backlight module with a second preset angle relative to the surface of the backlight module;

lighting the backlight module, and acquiring an image showing a light guide plate in the backlight module with a third preset angle relative to the surface of the backlight module; and illuminating the backlight module at the first preset angle with the external light source, and acquiring an image showing a diffusion plate or an optical film in the backlight module with a fourth preset angle relative to the surface of the backlight module.

12. The detection method of claim 11, wherein, the analyzing the acquired images that show the components in the backlight module so as to determine whether the defect present in the components in the backlight module includes:

performing a binarization processing on the acquired images that show the components in the backlight module, respectively, so as to obtain binary images correspondingly;

as for a group of N adjacent pixel points in each of the binary images, calculating a first average gray value of the group of the N adjacent pixel points, and calculating a second average gray value of all pixel points in a same row or in a same column as the group of the N adjacent pixel points, wherein N is a positive integer;

determining contrast variability between the first average gray value and the second average gray value; and when it is judged that the contrast variability is greater than a threshold, determining that the group of the N adjacent pixel points is the defect.

13. The detection method of claim 12, wherein, after determining that the defect presents in the components of the backlight module, the detection method further includes:

calculating geometrical feature parameters of at least one feature pattern formed by all defects present in the components in the backlight module; and determining a defect type of the feature pattern according to the calculated geometrical feature parameters of the feature pattern.

* * * * *